US011510725B2

(12) United States Patent
Sims et al.

(10) Patent No.: US 11,510,725 B2
(45) Date of Patent: Nov. 29, 2022

(54) ELECTROSURGICAL FORCEPS

(71) Applicant: COVIDIEN LP, Mansfield, MA (US)

(72) Inventors: Grant T. Sims, Boulder, CO (US);
Kelley D. Goodman, Erie, CO (US);
Craig V. Krastins, Arvada, CO (US);
Robert F. McCullough, Jr., Boulder, CO (US); Jennifer L. Rich, Parker, CO (US); Daniel W. Mercier, Erie, CO (US)

(73) Assignee: Covidien LP, Mansfield, MA (US)

( * ) Notice: Subject to any disclaimer, the term of this patent is extended or adjusted under 35 U.S.C. 154(b) by 673 days.

(21) Appl. No.: 16/262,389

(22) Filed: Jan. 30, 2019

(65) Prior Publication Data

US 2020/0237432 A1 Jul. 30, 2020

(51) Int. Cl.
*A61B 18/14* (2006.01)
*A61B 18/00* (2006.01)

(52) U.S. Cl.
CPC .. *A61B 18/1442* (2013.01); *A61B 2018/0063* (2013.01); *A61B 2018/00184* (2013.01); *A61B 2018/00589* (2013.01); *A61B 2018/00595* (2013.01); *A61B 2018/00601* (2013.01); *A61B 2018/00916* (2013.01); *A61B 2018/1455* (2013.01)

(58) Field of Classification Search
CPC ............ A61B 18/1442; A61B 18/1445; A61B 2018/00184; A61B 2018/00589; A61B 2018/00595; A61B 2018/00601; A61B 2018/0063; A61B 2018/00916
See application file for complete search history.

(56) References Cited

U.S. PATENT DOCUMENTS

| | | | |
|---|---|---|---|
| 5,219,354 A | 6/1993 | Choudhury et al. |
| 5,447,265 A | 9/1995 | Vidal et al. |
| 5,499,997 A | 3/1996 | Sharpe et al. |
| 5,797,938 A | 8/1998 | Paraschac et al. |
| 5,860,975 A | 1/1999 | Goble et al. |
| 6,603,100 B2 | 8/2003 | Wilkins et al. |
| 7,207,472 B2 | 4/2007 | Wukusick et al. |
| 7,297,136 B2 | 11/2007 | Wyrick |
| 7,550,975 B2 | 6/2009 | Honda et al. |
| 7,819,299 B2 | 10/2010 | Shelton, IV et al. |
| 8,197,479 B2 | 6/2012 | Olson et al. |
| 8,343,151 B2 | 1/2013 | Siebrecht et al. |
| 8,388,646 B2 | 3/2013 | Chojin |
| 8,480,671 B2 | 7/2013 | Mueller |
| 8,568,412 B2 | 10/2013 | Brandt et al. |
| 8,628,557 B2 | 1/2014 | Collings et al. |

(Continued)

FOREIGN PATENT DOCUMENTS

| | | |
|---|---|---|
| DE | 102010013060 A1 | 9/2011 |
| DE | 202012013219 U1 | 11/2015 |
| WO | 2009153015 A1 | 12/2009 |

*Primary Examiner* — Michael F Peffley
*Assistant Examiner* — Bo Ouyang
(74) *Attorney, Agent, or Firm* — Carter, DeLuca & Farrell LLP (57) ABSTRACT

An electrosurgical forceps includes a pair of first and second shaft members pivotably coupled to one another, an end effector assembly coupled to the pair of first and second shaft members, a knife, and a knife deployment mechanism. The knife deployment mechanism has one or more safety features that resist an inadvertent deployment of the knife.

14 Claims, 5 Drawing Sheets

(56) References Cited

U.S. PATENT DOCUMENTS

| | | |
|---|---|---|
| 8,679,115 B2 | 3/2014 | Reschke |
| 8,696,665 B2 | 4/2014 | Hunt et al. |
| 8,752,264 B2 | 6/2014 | Ackley et al. |
| 8,920,461 B2 | 12/2014 | Unger et al. |
| 8,968,313 B2 | 3/2015 | Larson |
| 8,973,805 B2 | 3/2015 | Scirica et al. |
| 9,345,534 B2 | 5/2016 | Artale et al. |
| 9,610,114 B2 | 4/2017 | Baxter, III et al. |
| 9,675,405 B2 | 6/2017 | Trees et al. |
| 9,707,029 B2 | 7/2017 | Nobis et al. |
| 9,877,775 B2 | 1/2018 | Hart |
| 2001/0045442 A1 | 11/2001 | Whitman |
| 2004/0094597 A1 | 5/2004 | Whitman et al. |
| 2007/0043352 A1* | 2/2007 | Garrison .............. A61B 17/285 606/51 |
| 2007/0173814 A1 | 7/2007 | Hixson et al. |
| 2010/0286691 A1 | 11/2010 | Kerr et al. |
| 2011/0054468 A1 | 3/2011 | Dycus |
| 2012/0197253 A1 | 8/2012 | Nishimura et al. |
| 2012/0265241 A1 | 10/2012 | Hart et al. |
| 2013/0296843 A1 | 11/2013 | Boudreaux et al. |
| 2014/0005704 A1 | 1/2014 | Vakharia et al. |
| 2014/0276738 A1 | 9/2014 | Price et al. |
| 2014/0276970 A1 | 9/2014 | Messerly et al. |
| 2014/0309665 A1 | 10/2014 | Parihar et al. |
| 2015/0272660 A1 | 10/2015 | Boudreaux et al. |
| 2016/0135868 A1 | 5/2016 | Joseph et al. |
| 2016/0157922 A1* | 6/2016 | Lee .................... A61B 18/1442 606/51 |
| 2016/0157923 A1* | 6/2016 | Ding .................. A61B 18/1442 606/51 |
| 2016/0166256 A1 | 6/2016 | Baxter, III et al. |
| 2017/0196629 A1 | 7/2017 | Nagtegaal |
| 2017/0238991 A1 | 8/2017 | Worrell et al. |
| 2017/0245933 A1 | 8/2017 | Graham et al. |
| 2017/0367752 A1 | 12/2017 | Boudreaux et al. |

* cited by examiner

ELECTROSURGICAL FORCEPS

BACKGROUND

The present disclosure relates to electrosurgical instruments and, more particularly, to electrosurgical forceps for grasping, treating, and/or dividing tissue.

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue.

Typically, once tissue is treated, the surgeon has to accurately sever the treated tissue. Accordingly, many electrosurgical forceps have been designed which incorporate a knife configured to effectively sever tissue after treating the tissue.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

As used herein, the terms parallel and perpendicular are understood to include relative configurations that are substantially parallel and substantially perpendicular up to about +/−10 degrees from true parallel and true perpendicular.

An electrosurgical forceps provided in accordance with aspects of the present disclosure includes a pair of first and second shaft members pivotably coupled to one another, an end effector assembly coupled to the pair of first and second shaft members and configured to move between an open configuration and a closed configuration in response to pivoting of the first and second shaft members, a knife selectively translatable through the first shaft member from a retracted position to an extended position in which the knife extends at least partially through the end effector assembly, and a knife deployment mechanism. The knife deployment mechanism includes a trigger rotatably coupled to the first shaft member, and a crank disposed within the first shaft member. The crank has a first end portion coupled to the trigger and a second end portion operably coupled to the knife, such that a rotation of the crank by the trigger deploys the knife. The first shaft member has a detent configured to resist a rotation of the crank.

In aspects, the crank may be configured to overcome the resistance of the detent of the first shaft member upon an application of a threshold actuation force on the trigger.

In some aspects, the detent of the first shaft member may block a path of the crank to resist movement of the crank.

In further aspects, the detent of the first shaft member may be flexible, such that upon an application of a threshold actuation force on the trigger, the detent flexes out of the path of the crank.

In other aspects, the crank may have a protrusion extending from an end portion thereof. The protrusion of the crank and the detent of the first shaft member may overlap with one another.

In aspects, the protrusion of the crank may be configured to move over the detent of the first shaft member upon an application of a threshold actuation force on the trigger.

In some aspects, the detent and/or the protrusion may be flexible, such that the detent or the protrusion flexes out of the way of the other upon an application of a threshold actuation force on the trigger.

In further aspects, the first shaft member may include an outer housing. The detent may extend inwardly from the outer housing of the first shaft member.

In other aspects, the knife deployment mechanism may include a linkage having a proximal end portion operably coupled to the crank, and a pivot pin rotatably supported by a distal end portion of the linkage and coupled to the knife. The knife may be configured to move between the retracted and extended positions in response to an actuation of the trigger.

In aspects, the crank may have a first end portion coupled to the trigger and a second end portion rotatably coupled to the proximal end portion of the linkage.

In some aspects, the crank may rotate in response to an actuation of the trigger to rotate and translate the linkage.

In accordance with another aspect of the present disclosure, an electrosurgical forceps is provided and includes a pair of first and second shaft members pivotably coupled to one another, an end effector assembly coupled to the pair of first and second shaft members and configured to move between an open configuration and a closed configuration in response to pivoting of the first and second shaft members, a knife selectively translatable through the first shaft member from a retracted position to an extended position in which the knife extends at least partially through the end effector assembly, and a knife deployment mechanism. The knife deployment mechanism includes a trigger rotatably coupled to the first shaft member and operably coupled to the knife, such that a rotation of the trigger deploys the knife. The first or second shaft member has a detent configured to interact with the trigger to resist a rotation of the trigger.

In aspects, the detent may be movable relative to the trigger from a first position, in which the detent resists rotation of the trigger, and a second position, in which the detent allows rotation of the trigger.

In some aspects, the detent and the trigger may interlock with one another when the detent is in the first position.

In further aspects, the detent may be configured to move axially between the first and second positions.

In other aspects, the detent may be configured to move rotationally between the first and second positions.

In aspects, the first and second shaft members may each include an outer housing. The detent may extend outwardly from the outer housing of the first shaft member or the outer housing of the second shaft member.

In some aspects, the knife deployment mechanism may include a crank having a first end portion coupled to the trigger, a linkage having a proximal end portion operably coupled to a second end portion of the crank, and a pivot pin rotatably supported by a distal end portion of the linkage and coupled to the knife. The knife may be configured to move between the retracted and extended positions in response to an actuation of the trigger.

In accordance with yet another aspect of the present disclosure, an electrosurgical forceps is provided and includes a pair of first and second shaft members pivotably coupled to one another, an end effector assembly coupled to the pair of first and second shaft members and configured to move between an open configuration and a closed configuration in response to pivoting of the first and second shaft members, a knife selectively translatable through the first shaft member from a retracted position to an extended position in which the knife extends at least partially through the end effector assembly, and a knife deployment mechanism. The knife deployment mechanism includes a first trigger rotatably coupled to the first shaft member and operably coupled to the knife, and a second trigger configured to move relative to the first trigger from a first position to a second position, in which the second trigger engages the first trigger, such that a further movement of the second trigger drives a rotation of the first trigger to deploy the knife.

In aspects, the first trigger may be configured to remain stationary relative to the first shaft member during movement of the second trigger from the first position to the second position.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
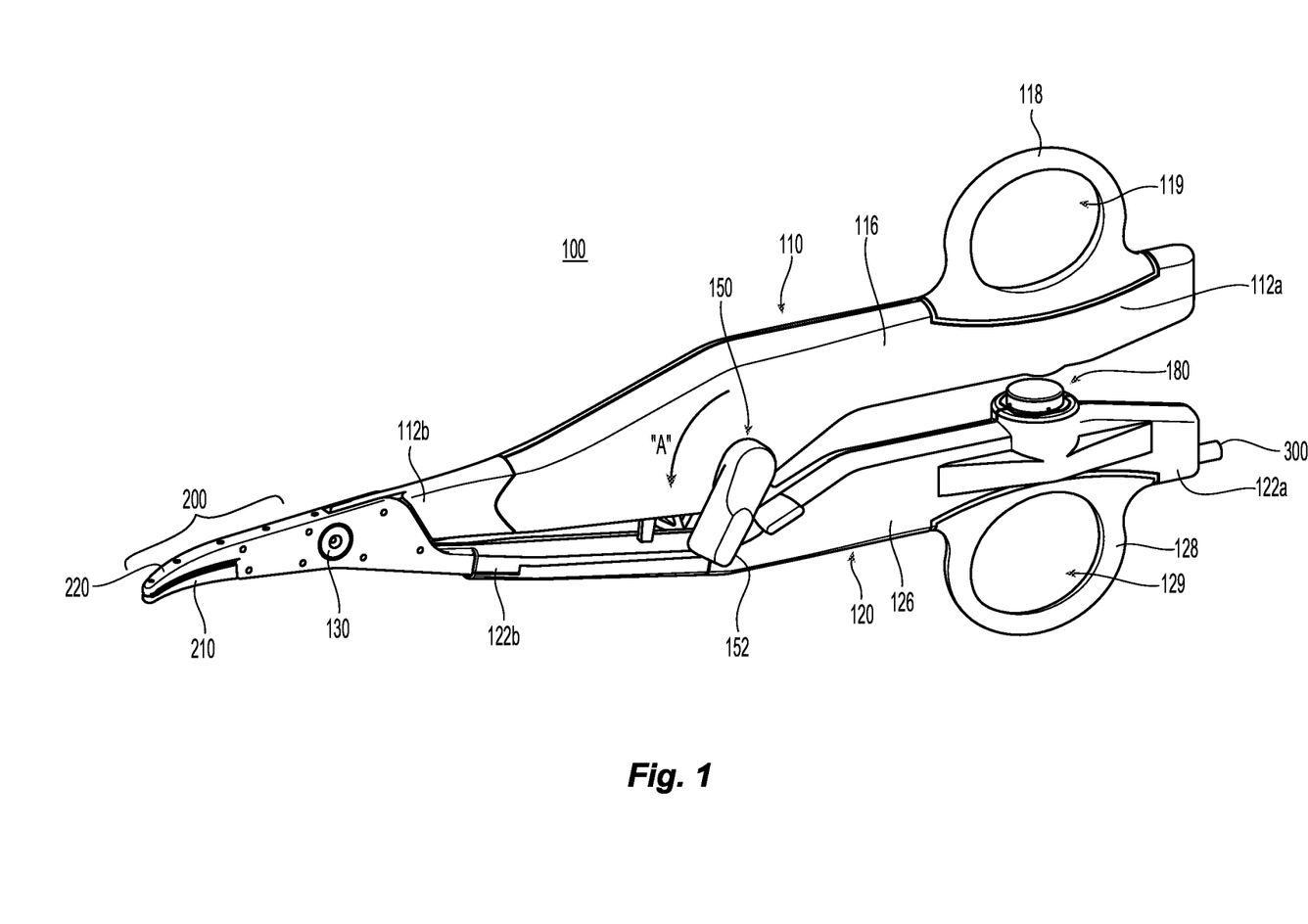
FIG. 1 is a side, perspective view of an electrosurgical forceps provided in accordance with aspects of the present disclosure.
Figure 2:
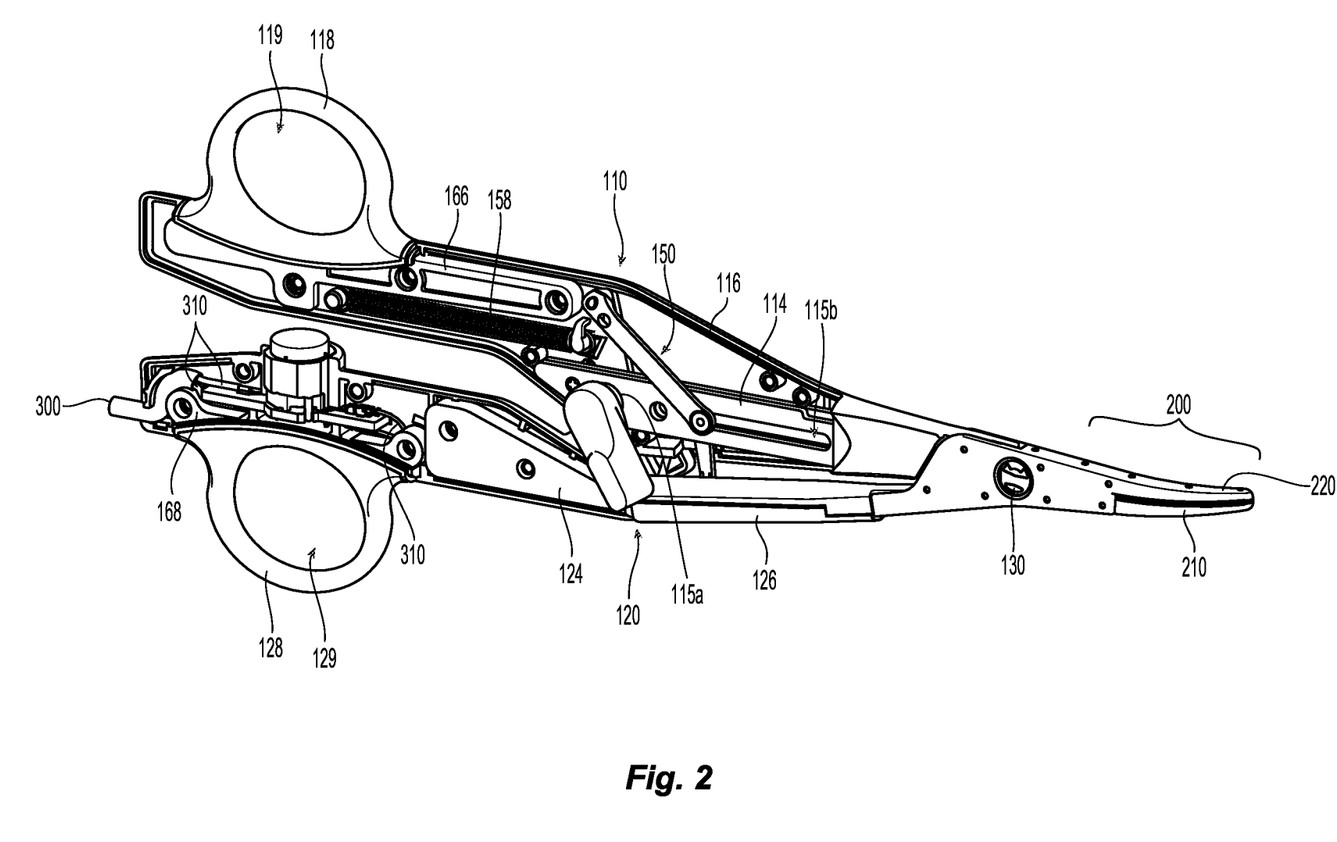
FIG. 2 is a perspective view from one side of the forceps of FIG. 1 with portions of outer housings of first and second shaft members removed to illustrate the internal components therein.

Referring to FIGS. 1 and 2, a forceps 100 provided in accordance with the present disclosure generally includes first and second shaft members 110, 120 and an end effector assembly 200. Shaft members 110, 120 each have a proximal end portion 112a, 122a and a distal end portion 112b, 122b. End effector assembly 200 includes first and second jaw members 210, 220 extending from distal end portions 112b, 122b of first and second shaft members 110, 120, respectively. Forceps 100 further includes a pivot member 130 pivotably coupling first and second shaft members 110, 120 with one another, a knife 140 (FIG. 3), a knife deployment mechanism 150 for selectively deploying knife 140, and a switch assembly 180 for enabling the selective supply of electrosurgical energy to end effector assembly 200. An electrosurgical cable 300 electrically couples forceps 100 to a source of energy (not shown), e.g., an electrosurgical generator, to enable the supply of electrosurgical energy to jaw members 210, 220 of end effector assembly 200 upon activation of switch assembly 180.

Each shaft member 110, 120 includes an inner frame 114, 124, an outer housing 116, 126 surrounding at least a portion of the respective inner frame 114, 124, and a handle 118, 128 engaged with the respective outer housing 116, 126 towards proximal end portions 112a, 122a of first and second shaft members 110, 120, respectively. Inner frame 124 of second shaft member 120 and inner frame 114 of first shaft member 110 are pivotably coupled to one another via pivot member 130 such that shaft members 110, 120 are movable relative to one another between spaced-apart and approximated positions to thereby pivot jaw members 210, 220 relative to one another between open and closed positions.

Outer housings 116, 126 of first and second shaft members 110, 120 enclose and/or operably support the internal components disposed within first and second shaft members 110, 120. More specifically, outer housing 116 of first shaft member 110 encloses and supports at least a portion of inner frame 114 and knife deployment mechanism 150, while outer housing 126 of shaft member 120 receives electrosurgical cable 300 and encloses and supports at least a portion of inner frame 124, switch assembly 180, and the lead wires 310 of electrosurgical cable 300. Handles 118, 128 are engaged with outer housings 116, 126 towards proximal end portions 112a, 112b of first and second shaft members 110, 120 and extend outwardly from first and second shaft members 110, 120. Handles 118, 128 define finger holes 119, 129 configured to facilitate grasping and manipulating shaft members 110, 120.

Figure 4:
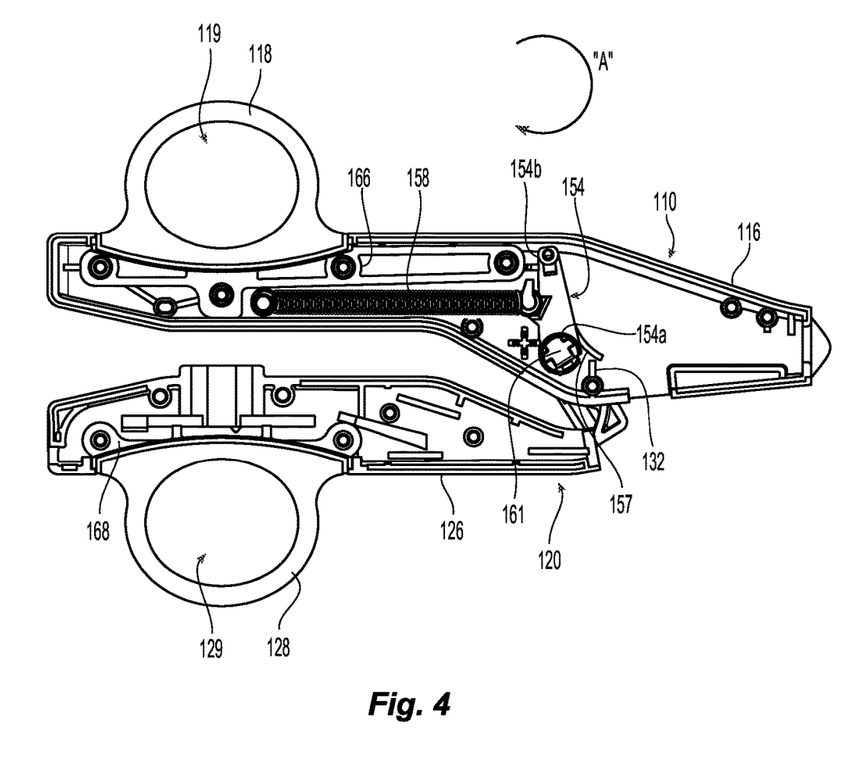
FIG. 4 is a side view of the forceps, with parts removed, illustrating a pair of detents of the knife deployment mechanism.

With brief reference to FIG. 4, first shaft member 110 has a detent 132 extending from outer housing 116 thereof. Detent 132 may be a rectangular-shaped protuberance or assume any suitable shape. In some aspects, detent 132 may extend from inner frame 114 of first shaft member 110 or any other stationary component of first shaft member 110. It is contemplated that detent 132 may be monolithically formed with outer housing 116 or connected thereto. Detent 132 may be fabricated from a flexible material (e.g., an elastomer) configured to flex or deform relative to and out of an arcuate path defined by a crank 154 of blade deployment mechanism 150 upon crank 154 imparting a threshold force on detent 132, as will be described below.

Figure 3:
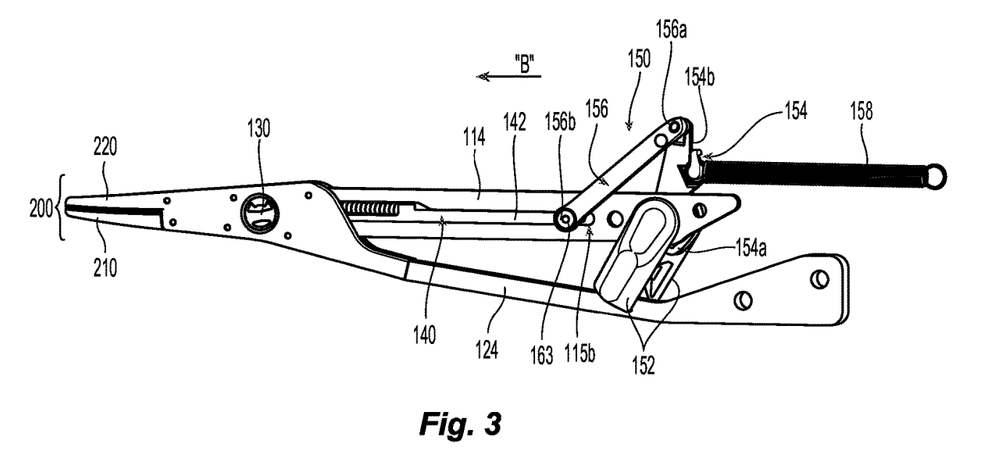
FIG. 3 is a side, perspective view of the forceps of FIG. 1 with portions removed to illustrate a knife and a knife deployment mechanism.

With reference to FIGS. 2-4, knife deployment mechanism 150 is coupled to first shaft member 110 and generally includes a pair of opposed triggers 152 extending from either side of first shaft member 110, crank 154, a linkage 156, and a biasing member 158. Knife deployment mechanism 150 is disposed within outer housing 116 of first shaft member 110 with the exception of opposed triggers 152, which extend from either side of outer housing 116. Triggers 152 are rotatably coupled to inner shaft 114 of first shaft member 110 and are typically actuated by fingers of a user. Crank 154 is configured for positioning on one side of inner frame 114 of shaft member 110 and includes a pair of integral (or otherwise engaged) pivot bosses 161 (only one pivot boss explicitly shown) extending from either side thereof at a first end portion 154a of crank 154. A first pivot boss (not explicitly shown) of crank 154 extends through a trigger aperture 115a defined in inner frame 114 (see FIG. 2) and through an aperture (not explicitly shown) defined through a first side of outer housing 116 of first shaft member 110 to enable engagement of one of the triggers 152. A second pivot boss 161 of crank 154 extends through an aperture (not explicitly shown) defined through a second side of outer housing 116 of first shaft member 110 to enable engagement of the other trigger 152 therewith, e.g., via press-fitting, adhesion, or other suitable engagement. As such, rotation of triggers 152 relative to first shaft member 110 drives rotation of crank 154 about first end portion 154a thereof.

Crank 154 is disposed adjacent detent 132 of outer housing 116 and moves, in response to a rotation of triggers 152, along a path that overlaps with detent 132. As such, upon an attempt at actuating triggers 152, a rotation of crank 154 about first end portion 154a thereof is resisted due to the engagement between crank 154 and detent 132 of outer housing 116. If the application of an actuation force on triggers 152 exceeds a threshold force, crank 154 deforms or flexes detent 132 of outer housing 116 out of the way crank's 154 arcuate path to allow crank 154 to rotate to deploy knife 140.

Crank 154 may have a protrusion 157 that extends outwardly from a first end portion 154a thereof. In some embodiments, protrusion 157 may extend from any suitable location of crank 154. Protrusion 157 of crank 154 and detent 132 of outer housing 116 are adjacent one another and, in some aspects, in contact with one another. As such, when a user attempts to actuate triggers 152, rotation of crank 154 about first end portion 154a is impeded due to the engagement between protrusion 157 of crank 154 and detent 132 of outer housing 116. If the application of an actuation force on triggers 152 exceeds the threshold force, protrusion 157 and/or detent 132 flexes or deforms to allow protrusion to pass over detent 132, thereby allowing crank 154 to rotate.

As shown in FIG. 3, linkage 156 of knife deployment mechanism 150 includes a proximal end portion 156a pivotably coupled to a second end portion 154b of crank 154. A distal end portion 156b of linkage 156 is pivotably coupled to knife 140 via pivot pin 163. Pivot pin 163 may be integrally formed with linkage 156, e.g., as a post extending therefrom, or may be a separate component from linkage 156. Pivot pin 163 extends transversely through a longitudinal slot 115b of inner frame 114 such that pivot pin 163 is constrained to longitudinal movement within longitudinal slot 115b. Linkage 156 is disposed on one side of inner frame 114, which may be the same side as crank 154 or the opposite side (as shown). In either configuration, pivot pin 163 extends from linkage 156 and through longitudinal slot 115b, whereby a portion of pivot pin 163 protrudes laterally from the opposite side of inner frame 114. Knife 140 includes a proximal body 142 configured to receive pin 163 to pivotably couple knife 140 to distal end portion 156b of linkage 156.

Biasing member 158 of knife deployment mechanism 150, e.g., an extension spring or other suitable biasing member 158, is engaged at a distal end portion thereof to crank 154 and at a proximal end portion thereof to a support plate 166 of outer housing 116 (FIG. 4). Support plate 166 includes handle 118 of shaft member 110 integrally formed therewith or otherwise engaged thereto, and may be secured within outer housing 116 in any suitable fashion, e.g., via protrusion-aperture engagement. Support plate 166 provides increased structural support to first shaft member 110 to inhibit splaying of first and second shaft members 110, 120 during use. Second shaft member 120 similarly includes a support plate 168 integrally formed with or otherwise engaging handle 128 of shaft member 120 and secured to outer housing 126, although support plate 168 need not extend distally as with support plate 166.

Biasing member 158 biases crank 154 towards a first orientation, corresponding to the un-actuated position of triggers 152 and the proximal-most position of linkage 156, thereby biasing knife 140 towards the retracted position. Upon rotation of either of triggers 152 relative to first shaft member 110, crank 154 is rotated against the bias of biasing member 158 to thereby urge linkage 156 distally such that pivot pin 163 is driven distally though longitudinal slot 115b to urge knife 140 from the retracted position towards an extended position, in which knife 140 extends through pivot member 130 and between jaw members 210, 220.

In use, proximal end portions 112a, 122a of first and second shaft members 110, 120 are approximated, thereby moving end effector assembly 200 to the closed configuration. With end effector assembly 200 in the closed configuration, a threshold actuation force is applied, in the direction indicated by arrow "A" in FIG. 1, to triggers 152 of knife deployment mechanism 150. The threshold actuation force is sufficient to bend protrusion 157 of crank 154 over detent 132 of outer housing 116, allowing second end portion 154b (FIG. 3) of crank 154 to rotate about first end portion 154a thereof. If the force applied to triggers 152 is below the threshold actuation force, such as when triggers 152 are inadvertently actuated, detent 132 of outer housing 116 remains in the path of protrusion 157 of crank 154, thereby preventing crank 154 from rotating.

Rotation of crank 154 rotates and translates linkage 156 of knife deployment mechanism 150. Since pivot pin 163 is supported by distal end portion 156b of linkage 156, pivot pin 163 translates with linkage 156, in the direction indicated by arrow "B" in FIG. 3, to urge the advancement of knife 140 toward the extended position.

To retract knife 140, crank 154 is released and/or the application of the threshold actuation force on triggers 152 is reduced, allowing the proximally-oriented bias of biasing member 158 to proximally urge knife 140 back toward the retracted position. It is contemplated that the force exerted on triggers 152 by biasing member 158 is sufficient to bend protrusion 157 of crank 154 back over detent 132 of outer housing 116 to return triggers 152 to the initial position.

Figure 5:
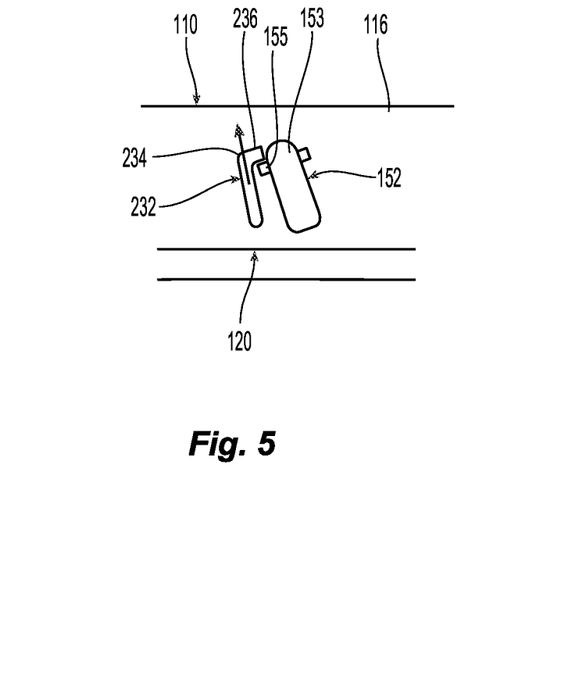
FIG. 5 is an enlarged, side view of the forceps illustrating a trigger and a movable detent in accordance with further aspects of the present disclosure.

With reference to FIG. 5, in another aspect of the present disclosure, instead of or in addition to forceps 100 having detent 132 (FIG. 4), first shaft member 110 of forceps 100 may have a detent 232 extending outwardly from outer housing 116 thereof. Detent 232 is coupled to outer housing 116 and is configured to move relative to outer housing 116 along a longitudinal axis of detent 232. Detent 232 may have an L-shaped configuration and be disposed adjacent one of triggers 152. Detent 232 has an end portion 234 configured to selectively engage with an end portion 153 of trigger 152. More particularly, end portion 153 of trigger 152 includes a laterally-extending protrusion 155, and end portion 234 of detent 232 includes a laterally-extending protrusion 236 in overlapping engagement with protrusion 155. In aspects, protrusions 155, 236 of trigger 152 and detent 232, respectively, may interlock using latches, friction-fit engagements, hook and loop fasteners, clips, hinges, snap-fit engagement, bayonet-type engagements, rotate and lock engagements, or the like.

In use, to deploy knife 140 (FIG. 3), detent 232 is first moved along outer housing 116 to separate protrusion 236 of detent 232 from protrusion 155 of trigger 152. With trigger 152 unlocked from detent 232, triggers 152 of knife deployment mechanism 150 may be actuated to deploy knife 140 in the manner described above. As such, actuation of knife 140 involves the first step of unlocking trigger 152 from detent 232, and the second step of actuating trigger 152, thus ensuring that actuation of knife 140 is performed only when intended.

Figure 6:
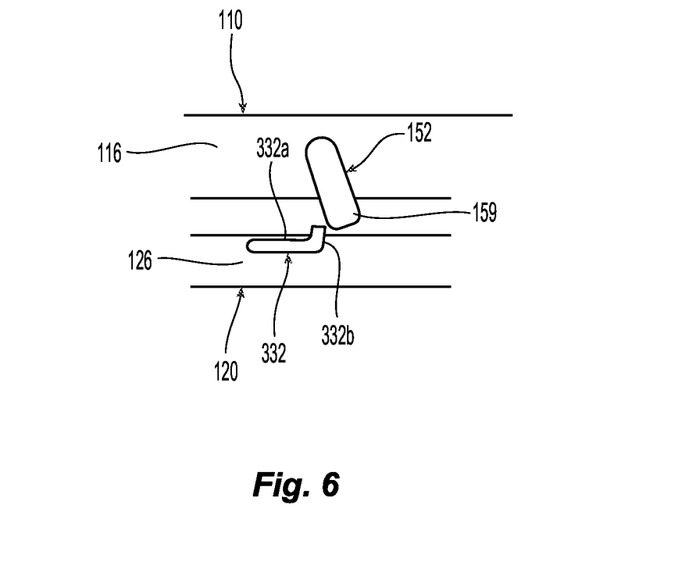
FIG. 6 is an enlarged, side view of the forceps illustrating a trigger and another movable detent in accordance with further aspects of the present disclosure.

With reference to FIG. 6, in another aspect of the present disclosure, in addition to or instead of forceps 100 having detent 132 (FIG. 4), second shaft 120 member of forceps 100 may have a detent 332 extending outwardly from outer housing 126 thereof. Detent 332 is coupled to outer housing 116 and is configured to rotate relative to outer housing 126 between a first position, in which detent 332 blocks an end portion 159 of trigger 152, and a second position out of trigger's 152 actuation path. In some aspects, detent 332 may be slidable between the first and second positions.

In use, to deploy knife 140 (FIG. 3), detent 332 is first rotated about a first end portion 332a thereof to move a second end portion 332b thereof out of engagement with end portion 159 of trigger 152. With second end portion 332b of detent 332 out of trigger's 152 path, triggers 152 of knife deployment mechanism 150 may be actuated to deploy knife 140 in the manner described above. As such, actuation of knife 140 involves the first step of moving detent 332 to the second position, and the second step of actuating trigger 152, thus ensuring that actuation of knife 140 is performed only when intended.

Figure 7:
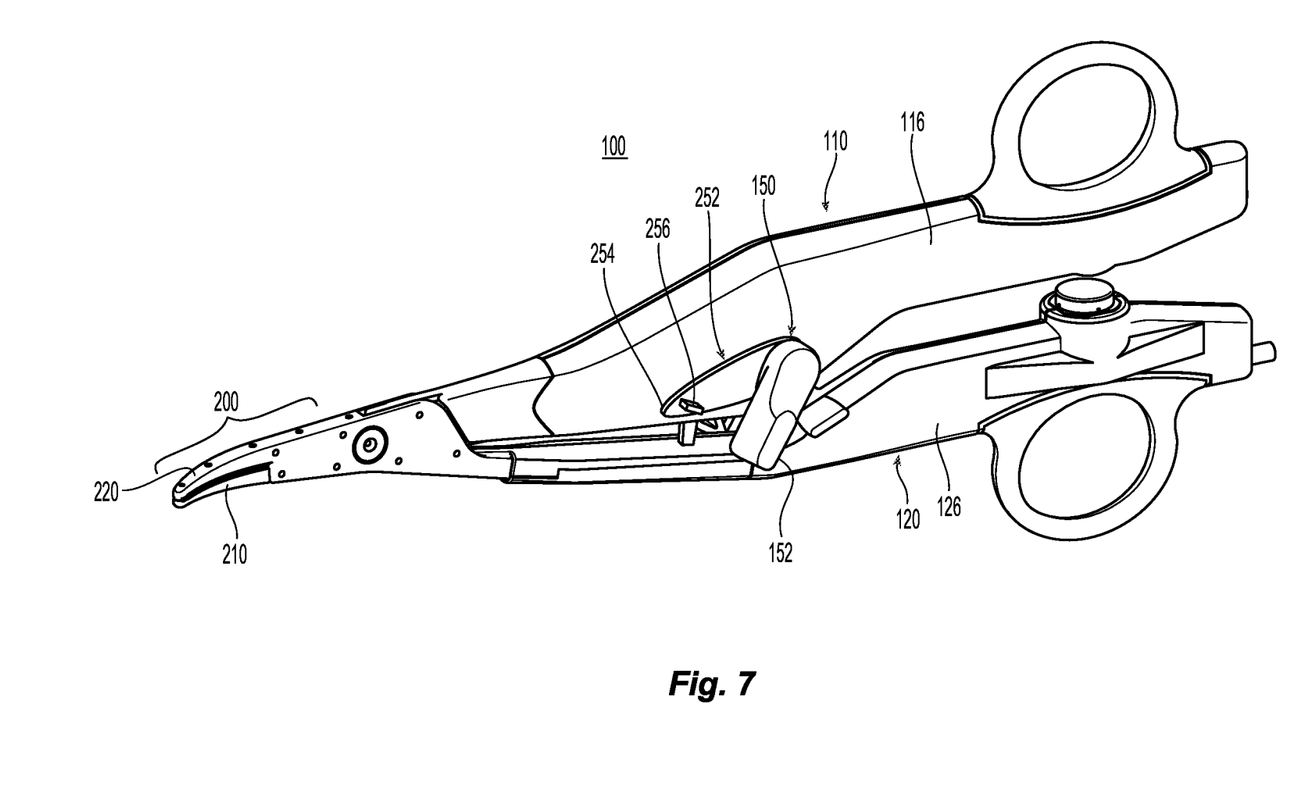
FIG. 7 is a side, perspective view of the forceps having a false trigger in accordance with aspects of the present disclosure.

With reference to FIG. 7, in yet another aspect of the present disclosure, knife deployment mechanism 150 of forceps 100 may include another trigger 252, referred to herein as a second trigger, disposed adjacent trigger 152 and rotatably coupled to outer housing 116. Second trigger 252 is configured to move relative to first trigger 152 from a first position to a second position. In the first or initial position, an end portion 254 of second trigger 252 is spaced from end portion 159 of trigger 152. Second trigger 252 has a catch 256 extending therefrom configured to engage trigger 152 upon rotating second trigger 252 to the second position. Catch 256 may be a protuberance that extends laterally outward from second trigger 252.

In use, to deploy knife 140 (FIG. 3), second trigger 252 is rotated from the first position to the second position, in which catch 256 of second trigger 252 engages trigger 152. As second trigger 252 is moved toward the second position, first trigger 152 remains stationary, and therefore does not yet deploy knife 140. After engaging second trigger 252 with trigger 152, continued rotation of second trigger 252 drives rotation of trigger 152 to deploy knife 140 in the manner described above. As such, actuation of knife 140 involves the first step of moving (e.g., rotating or sliding) second trigger 252 to the second position, and the second step of actuating trigger 152 via further movement of second trigger 252. It is contemplated that second trigger 252 may have a cover (not shown) that covers trigger 152 to prevent a user from directly accessing trigger 152.

For additional description of various components and manners of operating forceps 100 of the present disclosure, reference may be made to U.S. patent application Ser. No. 15/593,672, filed on May 12, 2017, the entire contents of which incorporated by reference herein.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416 (now U.S. Pat. No. 8,828,023), and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
  a pair of first and second shaft members pivotably coupled to one another;
  an end effector assembly coupled to the pair of first and second shaft members and configured to move between an open configuration and a closed configuration in response to pivoting of the first and second shaft members;
  a knife selectively translatable through the first shaft member from a retracted position to an extended position in which the knife extends at least partially through the end effector assembly; and
  a knife deployment mechanism including:
    a trigger rotatably coupled to the first shaft member; and
    a crank disposed within the first shaft member and having a first end portion coupled to the trigger and a second end portion operably coupled to the knife, such that rotation of the crank by the trigger deploys the knife, wherein the crank has a protrusion extending therefrom, the first shaft member having a detent configured to resist rotation of the crank, the crank being configured to overcome a resistance of the detent upon an application of a threshold actuation force on the trigger, the detent blocking a path of the protrusion of the crank to resist movement of the crank, wherein the detent is flexible, such that upon the application of the threshold actuation force on the trigger, the detent flexes or deforms out of the path of the protrusion of the crank.

2. The electrosurgical instrument according to claim 1, wherein the protrusion is configured to move over the detent upon the application of the threshold actuation force on the trigger.

3. The electrosurgical forceps according to claim 1, wherein the first shaft member includes an outer housing, the detent extending inwardly from the outer housing of the first shaft member.

4. The electrosurgical forceps according to claim 1, wherein the knife deployment mechanism includes:
   a linkage having a proximal end portion operably coupled to the crank; and
   a pivot pin rotatably supported by a distal end portion of the linkage and coupled to the knife, wherein the knife is configured to move between the retracted and extended positions in response to actuation of the trigger.

5. The electrosurgical forceps according to claim 4, wherein the crank has a first end portion coupled to the trigger and a second end portion rotatably coupled to the proximal end portion of the linkage.

6. The electrosurgical forceps according to claim 5, wherein the crank rotates in response to actuation of the trigger to rotate and translate the linkage.

7. An electrosurgical forceps, comprising:
   a pair of first and second shaft members pivotably coupled to one another;
   an end effector assembly coupled to the pair of first and second shaft members and configured to move between an open configuration and a closed configuration in response to pivoting of the first and second shaft members;
   a knife selectively translatable through the first shaft member from a retracted position to an extended position in which the knife extends at least partially through the end effector assembly; and
   a knife deployment mechanism including a trigger rotatably coupled to the first shaft member and operably coupled to the knife, such that a rotation of the trigger deploys the knife, wherein one of the first or second shaft members has a detent configured to interact with the trigger to resist rotation of the trigger, the trigger being configured to overcome a resistance of the detent upon an application of a threshold actuation force on the trigger, wherein the detent is configured to release the trigger after the application of the threshold actuation force on the trigger.

8. The electrosurgical forceps according to claim 7, wherein the detent is movable relative to the trigger from a first position, in which the detent resists rotation of the trigger, and a second position, in which the detent allows rotation of the trigger.

9. The electrosurgical forceps according to claim 7, wherein the first and second shaft members each include an outer housing, the detent extending outwardly from the outer housing of the first or second shaft member.

10. The electrosurgical forceps according to claim 7, wherein the knife deployment mechanism includes:
    a crank having a first end portion coupled to the trigger;
    a linkage having a proximal end portion operably coupled to a second end portion of the crank; and
    a pivot pin rotatably supported by a distal end portion of the linkage and coupled to the knife, wherein the knife is configured to move between the retracted and extended positions in response to the actuation of the trigger.

11. An electrosurgical forceps, comprising:
    a pair of first and second shaft members pivotably coupled to one another;
    an end effector assembly coupled to the pair of first and second shaft members and configured to move between an open configuration and a closed configuration in response to pivoting of the first and second shaft members;
    a knife selectively translatable through the first shaft member from a retracted position to an extended position in which the knife extends at least partially through the end effector assembly; and
    a knife deployment mechanism including:
       a first trigger rotatably coupled to the first shaft member and operably coupled to the knife; and
       a second trigger configured to move relative to the first trigger from a first position to a second position, in which the second trigger engages the first trigger, such that further movement of the second trigger drives rotation of the first trigger to deploy the knife, wherein the second trigger is disconnected from the end effector assembly such that the movement of the second trigger from the first position to the second position fails to cause movement of the end effector assembly between the open configuration and the closed configuration.

12. The electrosurgical forceps according to claim 11, wherein the first trigger is configured to remain stationary relative to the first shaft member during movement of the second trigger from the first position to the second position.

13. The electrosurgical forceps according to claim 11, wherein the first trigger is inaccessible to a user.

14. The electrosurgical forceps according to claim 11, wherein the first trigger is configured to remain stationary relative to the first shaft member as the second trigger moves from the first position to the second position.

* * * * *